United States Patent [19]

Ellis et al.

[11] 4,321,261

[45] Mar. 23, 1982

[54] IONIC OPHTHALMIC SOLUTIONS

[75] Inventors: Edward J. Ellis, Georgetown; Joseph C. Salamone, Marblehead, both of Mass.

[73] Assignee: Polymer Technology Corporation, Wilmington, Mass.

[21] Appl. No.: 51,961

[22] Filed: Jun. 25, 1979

Related U.S. Application Data

[63] Continuation-in-part of Ser. No. 38,703, May 14, 1979, abandoned, which is a continuation of Ser. No. 867,136, Jan. 5, 1978, Pat. No. 4,168,112.

[51] Int. Cl.³ .............................................. A61K 31/72
[52] U.S. Cl. ..................................... 424/180; 106/16; 424/78; 424/80; 424/81; 536/43; 536/56; 536/63; 536/66; 536/84; 536/96; 536/98; 536/120; 536/115; 524/556
[58] Field of Search ........................... 424/180, 80, 81; 106/16, 15 R; 260/29.6 H, 29.6 AT, 29.6 RW, 29.6 WB, 29.6 TA, 29.6

[56] References Cited

U.S. PATENT DOCUMENTS

| | | | |
|---|---|---|---|
| 2,451,645 | 10/1948 | Zienty et al. | 106/16 |
| 3,560,424 | 2/1971 | Glaser et al. | 260/29.6 RW |
| 3,808,178 | 4/1974 | Gaylord | 528/26 |
| 3,845,201 | 10/1974 | Haddad et al. | 424/180 |
| 3,870,791 | 3/1975 | Haddad et al. | 424/180 |
| 3,953,391 | 4/1976 | Dowbenko et al. | 260/29.6 TA |
| 3,963,662 | 6/1976 | Fujiwara et al. | 260/29.6 WB |
| 3,976,495 | 8/1976 | Buckman et al. | 106/15 R |
| 3,987,163 | 10/1976 | Rankin | 424/78 |
| 4,013,576 | 3/1977 | Loshaek | 252/106 |
| 4,026,712 | 5/1977 | Drury | 106/16 |
| 4,039,662 | 8/1977 | Hecht et al. | 424/180 |
| 4,102,842 | 7/1978 | Fujimoto et al. | 260/29.6 AT |
| 4,111,922 | 9/1978 | Beede et al. | 260/29.6 H |

*Primary Examiner*—Johnnie R. Brown
*Attorney, Agent, or Firm*—Wolf, Greenfield & Sacks

[57] ABSTRACT

A contact lens solution is provided for wetting, soaking and lubricating of hard contact lenses, particularly those carrying an ionic charge. The solution contains an ionic polymer of cationic or anionic charge that interacts with an oppositely charged surface of a contact lens forming an interfacial polyelectrolyte complex. This polyelectrolyte complex provides increased, long lasting lens wettability leading to a cushioning and lubricating effect with the eyelid and the cornea.

8 Claims, No Drawings

IONIC OPHTHALMIC SOLUTIONS

RELATED APPLICATIONS

This application is a continuation-in-part of U.S. application Ser. No. 38,703 filed May 14, 1979 now abandoned, which is in turn a continuation of parent application Ser. No. 867,136 filed Jan. 5, 1978, now U.S. Pat. No. 4,168,112.

BACKGROUND OF THE INVENTION

It has long been known in the art that a contact lens must have surfaces that have a certain degree of hydrophilicity in order to be wet by tears thus providing unblurred vision.

Soft, hydrophilic contact lenses, in addition to being wettable, provide comfort to the wearer but lack the ability to correct certain visual deficiencies such as astigmatism since they tend to conform to the shape of the corneal surface.

Often hydrophilic monomers can be added to a mixture of comonomers in the formation of contact lenses so that upon polymerization optically clear contact lenses result which have a certain degree of hydrophilicity. As the hydrophilic monomer content increases where it is added directly to the lens composition, the physical characteristics of the lenses are affected by the increased hydration propensity of the polymeric composition.

In some cases, it has been known to treat a formed contact lens with a polymerizable hydrophilic monomer to form a surface coating of hydrophilic polymer grafted to an otherwise hydrophobic polymer surface. Although effective, this method of increasing the hydrophilic character of the lens surface can suffer from involved and difficult manufacturing procedures as well as lack of permanence.

Present rigid and soft contact lenses sometimes retain water on their surfaces through secondary chemical bonding and as a consequence only a very thin layer of water molecules is present between the eye and the contact lens.

Soft lenses are inherently comfortable but often times, as with hard lenses, suffer from brief surface dryness between eye blinks. State of the art technology teaches that a water soluble neutral polymer may be applied to the surfaces of a hard contact lens to provide a "cushion" layer between the lens and the eye which is equated with increased wettability as well as wearer comfort and tolerance.

Dissipation of the "cushion" layer occurs rapidly in most prior art constructions, since there is little specific interaction between the mobile polymer in this layer and the lens surface. As a result the wearer begins to feel discomfort and must rewet the lens surfaces.

SUMMARY OF THE INVENTION

It is an object of this invention to provide a hard or soft synthetic polymer contact lens whose surface carries a thin layer of polyelectrolyte complex coating the lens surface and electrostatically bound thereto.

It is another object of this invention to provide a method of rendering a contact lens that has an ionic surface more compatible with the eye by immersing the lens in a solution of an oppositely charged ionic polymer to form a thin polyelectrolyte complex on the lens surface, which complex increases its hydrophilic character for a greater period of time relative to an untreated surface and which reduces the tendency for mucoproteins, a normal constituent of lacrimal tears, to adhere to a lens surface.

It is also an object of this invention to provide contact lens solutions, suitable for use in the human eye, which will interact with the surface of a hard or soft synthetic polymer contact lens thus forming a thin layer or coating of polyelectrolyte complex on the lens surface and electrostatically bound thereto.

It is a further object of this invention to provide a method of rendering a contact lens that has an ionic surface more wettable by dropping or rubbing an ophthalmic solution containing a hydrophilic polymer of opposite charge onto the lens surface.

The layer or coating comprises a polyelectrolyte complex which is formed by reaction of an ionic lens surface with an oppositely charged ionic polymer, and this complex forms a hydrogel at the lens surface which absorbs water, has good water retention, and is compatible with the physiological structures of the eye. A durable "cushion" is formed with provides long lasting comfort to the eye.

In the preferred embodiment, the lens is an oxygen permeable hard lens which carries an ionic charge or has the potential of having an ionic charge.

Preferably the charge of the lens surface is anionic, while that of the polymer in the ophthalmic solution is a cellulosic polymer of cationic charge. The cellulosic polymer should be compatible with the eye, should be non-irritating and yet should form a hydrogel which is electrostatically bound to the surface of the contact lens.

Preferably the lens coating is formed by merely immersing the lens in a solution which consists essentially of an ionic polymer dissolved in a water solution or a water solution containing soluble organic components comprising from 0.001 to 10% by weight of the solution. The ionic polymer can be any ionic polymer compatible with the eye and which does not cause eye irritation yet which forms a hydrogel and which is electrostatically bound to the surface of the contact lens.

It is a feature of this invention that thin coatings of from 20 to 2,500 Angstroms are formed, which coatings not only increase the compatibility of contact lens with the eye but also add a cushioning effect between the lens and the eye. Such coatings can reduce problems of punctate staining and further enhance the ability of the contact lens to be worn in the eye for periods up to 24 hours or more.

Depending on the concentration of ionic sites on the lens surface and the concentration of oppositely charged ionic polymer with which the surface is reacted, either wetting, soaking, or lubricating solutions can be prepared to provide optimal wearer comfortability. In addition, if cleaning agents are mixed with the ionic polymer solution, mucus, dirt and other unwanted deposits can be removed from the resulting polyelectrolyte complex surface.

DESCRIPTION OF PREFERRED EMBODIMENTS

Soft and hard synthetic polymer contact lens materials are normally prepared from neutral monomers and/or polymers. In this invention both soft and hard contact lens materials are prepared in such a manner that ionic sites are present on the lens surface, such sites can be reacted with a lens solution containing an oppositely charged, hydrophilic polymer. If the surface of the lens is considered polyanionic, the surface can then be reacted with a hydrophilic polycation with the resulting formation of a hydrophilic polyelectrolyte complex. Polyelectrolyte complexes have an equal amount of cations and anions, each obtained from a different source. In addition, these overall electrically neutral complexes exist as ionically cross-linked hydrogels that are effective in retaining water of hydration. In this invention, a surface coating of polyelectrolyte complex is achieved on a lens surface. A soft contact lens prepared entirely from a polyelectrolyte complex is known but would not have the desired properties of lenses preferred in accordance with this invention. In the present invention, it is possible that the reaction of ionic sites on a polymer surface, or potential ionic sites, with concommitant release of a low molecular weight electrolyte such as sodium chloride, hydrogen chloride, sodium sulfate, sodium methyl sulfate or any other related electrolyte could give rise to a monolayer coating of polyelectrolyte complex.

Polyelectrolyte complexes, although highly hydrophilic, are water-insoluble and can be dissolved with some difficulty usually by a ternary solvent system incorporating water, a water-soluble organic compound, and a low molecular weight electrolyte. This solubility behavior implies that in the present invention the polyelectrolyte complex treated surface is very difficult to dissolve and separate from the lens surface by the aqueous fluids of the eye, although this surface coating conceivably could be eroded by mechanical action in the eye during wear. Should dissipation of the polyelectrolyte complex from the lens surface occur, it can readily be replaced by re-treatment of the lens with the appropriate oppositely charged polyion solution.

The polyelectrolyte complex on the lens surface can be achieved by several means. If an anionic surface is desired, this can be accomplished by incorporation into the lens formulation of any monomer or monomers from the acrylate or methacrylate salt group, a vinyl sulfonate salt, an allyl or methallyl sulfonate or sulfate salt, a styrene sulfonate salt, an acryloyloxy ethyl or methacryloyloxyethyl sulfate salt, a substituted acrylamido or methacrylamido sulfonate salt or from related phosphonate, phosphate and phosphite salts of polymerizable monomers. Alternatively, a potentially anionic surface can be generated for subsequent treatment with a polycation followed by elimination of a low molecular weight acid (such as hydrogen chloride) or by subsequent treatment with a neutral basic polymer resulting in an acid-base neutralization reaction. Such anionic monomers include compounds such as acrylic and methacrylic acid, vinylsulfonic acid, allyl or methallyl sulfonic or sulfuric acid, styrene sulfonic acid, an acrylamido or methacrylamido sulfonic acid, or a polymerizable phosphonic or phosphoric acid.

If a cationic surface is desired, this is accomplished by incorporation into the lens formulation of any quaternary or protonated monomer or monomers from the acrylate or methacrylate salt group, a vinylpyridinium salt, a vinylimidazolium salt, a vinylimidazolinium salt, a vinylthiazolium salt, a vinylbenzylammonium salt, a diallyldialkylammonium salt, or a related alkylated or protonated polymerizable sulfonium or phosphonium salt. Alternatively, a potentially cationic surface can be generated for subsequent treatment with a polyacid resulting in an acid-base neutralization reaction. Such potentially cationic monomers include compounds such as a dialkylaminoethyl acrylate or methacrylate, a vinylpyridine, a vinylimidazole, a vinylbenzyl amine, a vinyl alkyl ether or sulfide, or a polymerizable vinyl phosphine.

It is also possible to generate an ionic charge on the lens surface by chemically or electrically modifying a neutral monomeric repeat unit to one that is charged. For example, an anionic surface can be obtained by treating a polyester material, such as polymethylmethacrylate, with an aqueous base, such as sodium hydroxide, to yield sodium methacrylate units on the lens surface. Alternatively, a polyester material can be hydrolyzed with an acid to yield methacrylic acid units on the lens surface which function as potential anionic sites. Similarly, a cationic surface can be obtained by alkylating or protonating a nucleophilic amine, sulfide or phosphine units on the lens surface.

A form of polyelectrolyte complex can be obtained through reaction of a polyacid surface with a solution of a hydrogen-bonding polymer such as polyvinylpyrrolidone or polyethylene oxide. Conversely, a hydrogen bonding surface can be treated with a polyacid. Such as polymer-polymer complex occurs through the hydrogen bonding of the polyacid with the acid-receptive groups of poly-N-vinylpyrrolidone or polyethylene oxide.

Virtually all hard and soft contact lens materials presently disclosed are electrically neutral polymers or copolymers. Such materials can be modified to include ionic surface groups. One general method for all types of lenses would include treatment of the surface with high energy irradiation in the presence of air to generate ionic surface groups, see A. Chaprio, *Radiation Chemistry of Polymeric Systems,* Vol. XV, Interscience, New York, 1962, and F. A. Makhlis, *Radiation Physics and Chemistry of Polymers,* Wiley and Sons, New York, 1975.

Another method would include modification of polymeric lenses formulations through incorporation of ionic (or potentially ionic) monomers. Polymethyl methacrylate, which is currently the material of choice in the hard lens area, is amenable to such modification. Examples of this approach include the copolymerization of either acrylic acid, methacrylic acid or dimethylaminoethyl methacrylate to provide a polymethyl methacrylate lens with ionic groups on the surface.

Another example would include the modification of oxygen permeable lens formulations such as those in U.S. Pat. No. 3,808,178. These formulations are copolymers of methyl methacrylate with a siloxanyl alkyl ester of methacrylic acid and can be modified through the addition of either acrylic acid, methacrylic acid or dimethylaminoethyl methacrylate.

In a similar fashion the monomers acrylic acid, methacrylic acid or dimethylaminoethyl methacrylate could be employed as coreactants with hydroxyethyl methacrylate to produce a material that is suitable for soft contact lenses which, in addition, provides an ionic surface.

Cellulosic polymers such as cellulose acetate butyrate have found use as contact lenses materials which exhibit moderate oxygen permeability. Polymers of this type contain residual cellulose alcohol functionalities which can be utilized as modification sites. Reaction of sodium chloroacetate with the alcohol functionalities will result in pendent carboxylate groups along the polymer chain. Contact lenses produced from this modified CAB material would be inherently wettable with an ionic surface receptive to polyelectrolyte complex formation.

The synthetic resin lens preferably has a total ionic charge of from 0.001% to 10%. Thus from 0.001% to 10% of the surface area is charged and the charge density often is about 5%. The lens solutions of this invention are preferably in all cases USP sterile. The solutions are preferably aqueous isotonic solutions. Preferably they are water solutions containing ingredients common to lens solutions such as buffers, preservatives and viscosity modifiers and which carry from 0.001 to 10% by weight of a water soluble ionic polymer or polymers such as:

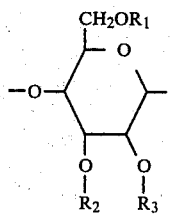

where $R_1$, $R_2$ and $R_3$ are selected from H, derivatives of $C_1$-$C_{20}$ carboxylic acid, $C_1$-$C_{20}$ alkyl groups, $C_1$ to $C_3$ monohydric and dihydric alkanols, hydroxyethyl groups, hydroxypropyl groups, ethylene oxide groups, propylene oxide groups, phenyl groups "Z" groups and combinations thereof.

The nature of the "Z" groups is:
cationic
A. groups containing nitrogen

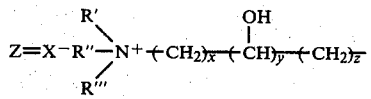

where:
R',R" and R''' can be H, $CH_3$, $C_2H_5$, $CH_2CH_2OH$ and

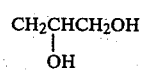

$X=0-5$, $y=0-4$, and $z=0-5$
$X^-=Cl^-, Br^-, I^-, HSO_4^-, CH_3SO_4^-, H_2PO_4^-, NO_3^-$
B. groups containing phosphorous

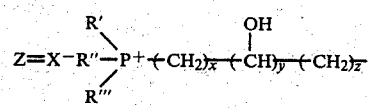

where:
R', R" and R''' can be H, $CH_3$, $C_2H_5$, $CH_2CH_2OH$ and

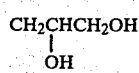

$X=0-5$, $y=0-4$ and $z=0-5$
$X^-=Cl^-, Br^-, I^-, HSO_4^-, CH_3SO_4^-, H_2PO_4^-, NO_3^-$ anionic
A. carboxylate containing groups

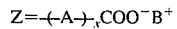

where:
$A=O$ or $R_1$
$B=Na^+, K^+, Li^+, \frac{1}{2}Ca^{+2}$
$X=0-5$
B. sulfonate containing groups

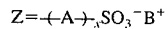

where:
$A=R_1$
$B=Na^+, K^+, Li^+, \frac{1}{2}Ca^{+2}$
C. Sulfate containing groups

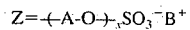

where:
$A=R_1$
$B=Na^+, K^+, Li^+, \frac{1}{2}Ca^{+2}$
$B=Na^+, K^+, Li^+, \frac{1}{2}Ca^{+2}$
$X=0-5$
D. phosphate containing groups

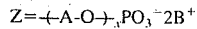

where:
$A=R_1$
$B=H^+, Na^+, K^+, Li^+, \frac{1}{2}Ca^{+2}$
$X=0-5$

Ionic cellulosic materials can also be prepared through grafting reactions by the addition of any homopolymers, copolymers or greater, onto any reactive position on the cellulose main chain or side chain substituent.

Mixtures of ionic polymers can be used in the solutions of this invention.

Other polymers useful as the ionic polymer or mixture of polymers include:

Cationic homopolymers, copolymers and graft polymers of:
N,N-dimethylaminoethyl acrylate and methacrylate
2-methacryloyloxyethyltrimethylammonium chloride and methylsulfate
2-,4-, and 2-methyl-5-vinylpyridine
2-,4-, and 2-methyl-5-vinylpyridinium chloride and methylsulfate
N-(3-methacrylamidopropyl)-N,N-dimethylamine
N-(3-methacrylamidopropyl)-N,N,N-trimethylammonium chloride
1-vinyl- and 2-methyl-1-vinylimidazole
1-vinyl- and 2-methyl-1-vinylimidazolium chloride and methylsulfate
N-(3-acrylamido-3-methylbutyl)-N,N-dimethylamine
N-(3-acrylamido-3-methylbutyl)-N,N,N-trimethylammonium chloride
N-(3-methacryloyloxy-2-hydroxylpropyl)-N,N,N-trimethylammonium chloride
diallyldimethylammonium chloride and methylsulfate vinylbenzyltrimethylammonium chloride
cationic starch
cationic poly-N-vinylpyrrolidone
cationic polyethylenimine
cationic polyacrylamide
cationic polyvinyl alcohol cationic guar gum
cationic cellulose
ionene polymers Anionic sodium carboxymethylcellulose
sodium carboxymethylhydroxyethylcellulose
sodium carboxymethylstarch
sodium carboxymethylhydroxyethylstarch
hydrolyzed polyacrylamide and polyacrylonitrile
homopolymers and copolymers of:
    acrylic and methacrylic acids
    sodium acrylate and methacrylate
    vinylsulfonic acid
    sodium vinylfulfonate
    p-styrenesulfonic acid
    sodium p-styrenesulfonate
    2-methacryloyloxyethylsulfonic acid
    3-methacryloyloxy-2-hyroxypropylsulfonic acid
    2-acrylamido-2-methylpropanesulfonic acid
    allylsulfonic acid
    2-phosphatoethyl methacrylate The ophthalmic solutions of this invention preferably contain an ionic cellulosic material such as, but not limited to:
a cellulose polymer containing N,N-dimethyl aminoethyl
groups either protonated or quaternized
a cellulose polymer containing 1-(N,N-dimethyl amino-2-hydroxyl
propyl)groups either protonated or quaternized
sodium cellulose acetate sulfate
sodium cellulose sulfate
sodium caboxy methyl cellulose
sodium cellulose phosphate Other additives to the soaking lens solutions of this invention include conventional lens solution cleaning and soaking solutions additives. Preservatives such as benzyalkonium chloride, ethylenediaminetetraacetic acid (EDTA) and salts thereof, mercurials, trichlorban and chlorobutanol can be used. Wetting agents or viscosity modifiers such as polyvinyl alcohol, hydroxypropyl methylcellulose hydroxy ethyl cellulose, polyvinyl pyrrolidine, polyethylene oxide and methyl cellulose can be used. Lubricating agents such as the wetting agents above but in known higher concentrations can be used. Soaking and cleaning agents such as neutral detergents including sodium dodecyl sulfate and neutral surfactants based on nonyl phenol can be used. Buffers include boric acid, sodium borate, phosphoric acid, disodium phosphate, sodium bicarbonate. Other conventional buffers, biocides and viscosity modifiers may also be used. The additives are used in a wide range of concentrations as known in the art. Preferably the pH of the solutions are as near to body pH as possible and always in the range of pH 6-8, particularly if the solution is to be used only to form the coating of this invention and is to be put directly in the eye when wearing the lens as an artificial tear. Otherwise the pH can vary widely. If used to soak a lens and if the solution is not of a physiological pH the lens can be washed and adjusted in pH before put in the eye. Preferably the solutions are aqueous although organic or other solvent solutions could be used.

While it is preferred to merely soak the lens in the solution at room temperature, the solution can also be sprayed, dropped, or rubbed on the lens surface.

The solutions are rendered sterile by methods common in the art, boiling, autoclaving, gamma irradiation or by membrane filtration.

In all cases it is preferred to form a coating of no more than 2,500 Å over the lens surface which acts as a hyrogel. The hydrogel formed by the polyelectrolyte complex is an ionically cross-linked polymer that absorbs large amounts of water and at least 10% of its own weight of water. The lenses tend to be nonirritating to the eye and can be worn for long periods of time.

Specific examples of this invention are given below but are not meant in any way to limit this invention.

EXAMPLE I

Hard polymeric test samples were prepared from methylmethacrylate (MMA) and also from a comonomer mixture of methyl methacrylate (MMA) and methacrylate acid (MA). A minor amount of tetraethyleneglycol dimethacrylate (TEGDM) was incorporated in both formulations as a cross-linking agent. The free radical initiator 2,2'-azobisisobutyronitrile (AIBN) was utilized to effect polymerization. The formulation components (shown in Table I in weight percent) were thoroughly mixed, transferred to test tubes, stoppered, degassed, the filled with nitrogen. The test tubes were placed in a water bath at 40° C. and allowed to polymerize for two days. The tubes were then placed in a 60° C. oven for an additional three days, after which the polymerized rods were removed from the tubes. The rods were then subjected to conditioning for approximately fifteen hours at 100° C. under vacuum to complete the polymerization process and relieve any mechanical stresses present. Test specimens, in the form of 3/16" by ½" discs, were machined from the conditioned rods. The flat machined surfaces of the discs were then highly polished to provide an appropriate surface for contact angle measurements.

Contact angles were determined on hydrated specimens after immersed in $H_2O$ for 2 days with the values representing the advancing water droplet angle on the polished surface. Lower angles are indicative of more wettable materials which can be attributed to a more polar surface either as a result of the chemical groups present or the presence of bound water molecules.

The significantly lower contact angle produced by surface treatment "B" clearly illustrates the embodiment of this invention. The cationic hydroxyethylcellulose is ionically bound to the surface carboxylate (anionic) groups producing a layer of polyelectrolyte complex which contains bound water.

TABLE I

| Composition (wt. percent reagent) | | | | Surface Treatment | Advancing Angle in degress |
| --- | --- | --- | --- | --- | --- |
| MMA | MA | TEGDM | AZO | | |
| 98.8 | — | 1.0 | 0.2 | none | 82–84 |
| 93.8 | 5 | 1.0 | 0.2 | none | 74–75 |
| 93.8 | 5 | 1.0 | 0.2 | A* | 77–78 |
| 93.8 | 5 | 1.0 | 0.2 | B** | 64–65 |

*Treatment "A" was a five minute immersion in a sodium carbonate water solution (pH = 10.7) followed by a thorough rinse with distilled water.
**Treatment "B" was initially identical to treatment "A" with a subsequent five minute immersion in a 0.1 weight percent cationic hydroxyethylcellulose (Union Carbide JR-125 resin) water solution at room temperature followed by a thorough rinse with distilled water.

EXAMPLE II

Using the experimental procedures described in Example I hard polymeric test samples were prepared from methyl methacrylate (MMA), methacryloyloxypropyl tris(trimethylsilyl) siloxane (TRIS) and methacrylic acid (MA). A minor amount of tetraethylene glycol dimethacrylate (TEGDM) was incorporated as a cross-linking agent. The free radical initiator 2,2'-azobisisobutyronitrile (AIBN) was utilized to effect polymerization. The concentration of reagents employed, surface treatments and contact angle values are presented in Table II. This particular formulation was chosen as typical of those presently utilized in the production of hard, oxygen permeable contact lenses.

The lower contact angles exhibited by samples when surface treated by method "B" or "C" demonstrates the applicability of this invention to polymeric materials suited for hard, oxygen permeable contact lens.

TABLE II

| Composition (wt. percent reagent) | |
|---|---|
| MMA | 59.4 |
| TRIS | 34.6 |
| MA | 4.9 |
| TEGDM | 0.9 |
| AZO | 0.2 |
| Surface Treatment | Advancing angle in degrees |
| none | 80–82 |
| "A" | 82–83 |
| "B" | 77–78 |
| "C"* | 78–79 |

*Treatment "C" was initially identical to treatment "A" with a subsequent five minute immersion in a 0.1 weight percent polyvinylbenzyl trimethyl ammonium chloride water solution followed by a thorough rinse with distilled water.

EXAMPLE III

Using the experimental procedures described in Example I hard polymer test samples were prepared from methyl methacrylate (MMA), methacryloyloxypropyl tris(trimethylsilyl) siloxane (TRIS) and dimethylaminoethyl methacrylate (DMAEM). A minor amount of tetraethylene glycol dimethacrylate (TEGDM) was incorporated as a crosslinking agent. The free radical initiator 2,2'-azobisisobutyronitrile (AIBN) was utilized to effect polymerization. The concentration of reagents employed, surface treatments and contact angle values are presented in Table III. This particular composition was chosen as typical of a material which could be utilized in the production of highly oxygen permeable, hard contact lenses.

This Example illustrates the incorporation of a cationic monomer in the polymer formulation which is receptive to treatment with an anionic polymer to form a surface layer of polyelectrolyte complex. This behavior demonstrates the versatility of the present invention in that either an anionic (Example I and II) or a cationic (Example III) monomer may be incorporated into a polymeric formulation which is capable of forming a polyelectrolyte complex with a polyion of the opposite charge.

TABLE III

| Composition (wt. percent reagent) | |
|---|---|
| MMA | 51.8 |
| TRIS | 42.4 |
| DMAEM | 4.7 |
| TEGDM | 0.9 |
| AZO | 0.2 |
| Surface Treatment | Advancing angle in degress |
| none | 83–84 |

TABLE III-continued

| | |
|---|---|
| "D"* | 84–85 |
| "E"** | 75–76 |
| "F"*** | 77–78 |

*Treatment "D" was a five minute immersion in a hydrochloric acid solution (pH = 3.0) followed by a thorough rinse with distilled water.
**Treatment "E" was a five minute immersion in a 0.1 weight percent polyacrylic acid water solution followed by a thorough rinse with distilled water.
***Treatment "F" was initially identical to treatment "D" with a subsequent five minute immersion in a 0.1 weight percent sodium polystyrenesulfonate water solution followed by a thorough rinse with distilled water.

EXAMPLE IV

The following tabulation presents the various molecular weight grades of a commercial water soluble, cationic, cellulosic polymer which has utility in this invention. The polymer is supplied by Union Carbide Corporation under the trade name "Polymer JR Resins".

| | JR-125 | JR-400 | JR-30 M |
|---|---|---|---|
| Brookfield viscosity at 25° C. centipoises, 2.0% by weight aqueous solution | 110–120 | 400–440 | 12,000–13,000 |
| percent nitrogen | 1.7–2.2 | 1.7–2.2 | 1.7–2.2 |

This polymer is believed to contain quaternized N,N-dimethyl amino groups along the cellulose polymer chain.

EXAMPLE V

| Solution composition | Percent by weight |
|---|---|
| Hydroxyethyl cellulose (medium viscosity grade) | 0.25 |
| U.C.C. JR-400 | 0.10 |
| benzalkonium chloride | 0.005 |
| sodium chloride | 0.75 |
| potassium chloride | 0.20 |
| trisodium EDTA | 0.10 |
| distilled, deionized water | balance to 100 |

The lens solution in this Example is produced by adding the hydroxyethyl cellulose to the water and stirring until solution is achieved. The JR-400 resin is then added, with stirring, and allowed to completely dissolve. The remaining ingredients are then added and the entire solution stirred an additional one hour. The lens solution is then rendered sterile by passing it through a membrane filter.

EXAMPLE VI

| Solution composition | Percent by weight |
|---|---|
| hydroxyethyl cellulsoe (medium viscosity grade) | 0.15 |
| U.C.C. JR-30 M | 0.10 |
| benzalkonium chloride | 0.005 |
| sodium chloride | 0.8 |
| sodium bicarbonate | 0.1 |
| disodium EDTA | 0.1 |
| distilled, deionized water | balance to 100 |

The lens solution is prepared by the method stated in Example V. This lens solution has an approximate pH value of 8.2

EXAMPLE VII

| Solution Composition | Percent by Weight |
| --- | --- |
| U.C.C. JR-125 | 0.20 |
| thimerosal | 0.005 |
| sodium chloride | 0.6 |
| disodium EDTA | 0.05 |
| distilled, deionized water | balance to 100 |

The lens solution is prepared by the method stated in Example V.

EXAMPLE VIII

| Solution Composition | Percent by Weight |
| --- | --- |
| methyl cellulose | 0.30 |
| methyl cellulose carboxylic acid | 0.10 |
| thimerosal | 0.004 |
| sodium chloride | 0.80 |
| potassium chloride | 0.15 |
| disodium EDTA | 0.1 |
| distilled, deionized water | balance to 100 |

The lens solution in this Example is produced by the method stated in Example V.

EXAMPLE IX

| Solution Composition | Percent by Weight |
| --- | --- |
| Polyvinyl alcohol | 1.00 |
| sodium cellulose acetate sulfate | 0.05 |
| benzalkonium chloride | 0.005 |
| sodium chloride | 0.80 |
| disodium EDTA | 0.10 |
| sodium dihydrogen phosphate | 0.65 |
| disodium hydrogen phosphate | 0.20 |
| distilled, deionized water | balance to 100 |

The lens solution is prepared by the method stated in Example V. This lens solution has an approximate pH value of 6.2.

EXAMPLE X

The wetting and soaking solution described in Example V was used by a number of patients wearing hard, gas permeable contact lenses. The lens material was similar to the composition described in Example II and contained 5% copolymerized methacrylic acid. In this manner the surface of the lens was rendered anionic and thus receptive to the cationic cellulose polymer in the lens solution.

These patients had previously used a variety of commercial contact lens wetting and storage solutions which contained only neutral polymers when present. After using the solution of this invention practically all subjects reported a significant improvement in their lens wearing comfort and enhanced ability to wear their lenses for longer periods of time. No subject reported that the prior commercial contact lens solution was superior to this invention in maintaining the wearing comfort of their contact lenses.

As further evidence of the usefulness of this invention a few patients were monitored closely for clinical indications of the benefits of the lens solution described in Example V. After using only commercial hard contact lens wetting and soaking solutions about 25% of these patients developed symptoms of eye irritation accompanied by the observed adhesion of fluorescein dye to the surface of the cornea and such symptoms and signs recurred each time the lenses were worn. The use of this invention for the overnight storage of their contact lenses immediately eliminated all symptoms of eye irritation and staining of the eye tissue with fluorescein dye, thereby signifying, subjectively and objectively, the reversal of previous contact lens intolerance.

This Example clearly demonstrates the ability of this invention to provide improved comfort and long lasting in the wearing of hard contact lenses.

EXAMPLE XI

The use of commercial contact lens solutions in conjunction with hard, gas permeable lenses similar in composition to those described in Example II provided marginal results for a number of patients. These patients noted an onset of blurred vision after wearing their contact lenses for a period of time. After being instructed to substitute the wetting and soaking solution described in Example V most subjects reported that the use of this invention significantly prolonged the duration of clarity of their contact lens corrected vision and many were able to wear their lenses all their waking hours without observing any blurred vision at all. This improvement was accompanied by a decrease in the drying of the front surface of the contact lenses between blinks as observed with an illuminating binocular microscope (slit lamp) designed for the purpose of studying the surface of the human eye.

This Example illustrates the utility of the novel lens solution in providing unblurred vision for long periods of time by improving the surface wetting characteristics of the lens.

EXAMPLE XII

Contact lens produced from siloxane containing polymers are known to interact with lipids and lipoproteins normally present in human tears. As a result, waxy deposits accumulate on the surfaces of such lenses after a period of weeks or months which reduces the surface wettability of the lens. This relates directly to reduced comfort of these lenses thereby compromising their tolerance and clarity. Such deposits are best visualized by studying rinsed and dried lenses against a black background with an illuminating binocular microscope and can be quantitated according to the surface area affected and deposit thickness (opaqueness).

Two groups of patients, one group using a variety of commercial wetting and soaking solutions and the other group using a solution of this invention (Example V) were followed for one year. It was observed that the contact lenses of patients using this invention developed a significantly lower incidence of surface deposits than those using the commercial solutions.

EXAMPLE XIII

The lens solution described in Example V was used as a wetting and soaking solution by patients wearing conventional polymethyl methacrylate contact lens. Most patients reported an improvement in the wearing comfort of their contact lenses as compared to that experienced when using a variety of commercially available contact lens wetting and soaking solutions. Though less dramatic than in those patients wearing the lenses described in Example X, the improvement in lens performance was nevertheless significant. No subject preferred any of the commercial contact lens solutions to that of this invention. One explanation for these observations is based on the fact that polymethyl methacrylate can undergo hydrolysis to produce methacrylic acid units on the polymer chain. Neutralization of the acid takes place in the eye or in most ophthalmic solutions which are buffered to the pH range of 6 to 8. The lens surface will then be slightly negative due to the presence of carboxylate groups. In the identical manner described in Example X the positively charged cellulose polymer contained in the solution of this invention binds to the surface of the lens. The surface wetability of the polymethyl methacrylate is improved and wearing comfort is thereby increased.

EXAMPLE XIV

The ocular lubricant solution described in Example VII was used, in the form of eye drops, by a group of subjects wearing hard contact lenses formulated to have a negatively charged surface (Example II). The subjects in this group were chosen on the basis of the excessive amount of mucous produced by their eyes (due to chronic allergies or other reasons). As a result of their condition the subjects tended to accumulate surface deposits on their contact lenses at a rapid rate causing discomfort and blurred vision. It was necessary that they periodically remove and clean their lenses during each day. Such subjects were instructed to instill one or two drops of the lubricant solution (Example VII) in their eyes as needed and without removal of the lenses. All patients reported that the use of ocular lubricant was as effective in re-establishing the comfort and clarity of their lenses as was the removal, cleaning and re-insertion steps previously used. Moreover, a majority of subjects reported that the use of the ocular lubricant drops to clean and rewet the lens surfaces in situ had a longer lasting effect than the removal and cleaning steps. Furthermore, only one of the subjects in this group who had previously used a variety of commercial eye drop preparations noted that the former eye drops were superior to the present invention. This was in contrast to the majority who reported that the present invention was superior in its effectiveness and duration of benefit as compared to the previously used commercial preparations.

EXAMPLE XV

The ocular lubricant solution described in Example VII was used by a group of subjects wearing conventional polymethyl methacrylate contact lenses and whose eyes produced excessive mucous. Though less dramatic than in those patients wearing contact lenses formulated to have a negative charged surface, the effectiveness of this invention in restoring the comfort and clarity of the lenses in situ was similar.

Examples I through III teach the method of forming a hydrophilic polyelectroltye complex on the surface of a solid polymer mass bearing either a positive or a negative charge by treating said surface with a solution containing a polymer bearing the opposite charge. Furthermore, the wetting properties of said surface are significantly improved by this treatment.

The cationic cellulose polymer given in Example IV is typical of those water soluble cellulosic polymers bearing either positive or negative charges through inclusion of ionic groups along the main polymer chain or on a grafted polymer chain.

The compositions of Examples V through IX exemplify the ophthalmic solutions of the present invention. Examples V through VII represent solutions containing a water soluble, cationic cellulose based polymer; while Examples VII and IX represent solutions containing a water soluble, anionic cellulose polymer. Such solutions are useful as contact lens solutions, particularly when used in conjunction with a contact lens bearing the opposite charge. This illustrates the practical application of the teachings of Examples I through III.

The solutions of Examples V through IX were selectively tested in contact lens wearers. Use of the wetting and soaking solution of Example V was found to provide improved and long lasting comfort to the wearers (Example X), improved surface wetting characteristics and unblurred vision (Example XI), and reduced the incidence of surface deposits on the lenses (Example XII). Furthermore, the solution of Example V was found to provide some measure of improved wearing comfort to wearers of conventional polymethyl methacrylate contact lenses (Example XIII).

The ocular lubricant solution of Example VII was found to be particularly effective for contact lens wearers who produce excessive amounts of mucous (Example XIV). Such wearers could re-establish the comfort and clarity of their lenses by periodically instilling one or two drops of the ocular lubricant solution. Moreover, the ocular lubricant solution of Example VII was found to impart a degree of comfort and clarity to the conventional polymethyl methacrylate contact lenses of problem mucous wearers (Example XV).

The specific Examples set forth in this disclosure are meant to provide a clear understanding of the invention. These Examples are merely illustrative and are not to be understood as limiting the scope and basic principles of the invention in any way.

In general, the polymeric material of the lens is preferably selected from the group comprising:

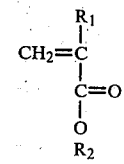

where $R_1=H$, $CH_3$, $CH_2COOH$, $CH_2COOCH_3$, or $CH_2COOC_6H_5$, and $R_2=H$, or $C_1-C_{20}$ derivative of a monohydric alkanol, a $C_1-C_3$ derivative of dihydric and trihydric alkanols, or

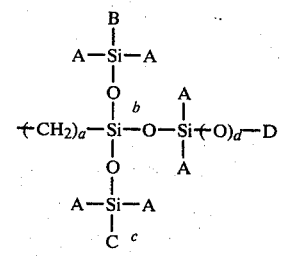

where "a" is an integer from one to three, "b" and "c" are integers from zero to two, "d" is an integer from zero to one, A is selected from the class of methyl and phenyl groups, B is selected from the class of methyl or phenyl groups, C and D represent either no group (cyclic ring from "c" to "d") or methyl or phenyl groups.

The polymeric material can also consist essentially of:

where R and R are selected from H, $CH_3$, $C_2H_5$, $C_3H_7$, $C_6H_5$, COOH, $CH_2=CH-$ and $-O-$ groups.

In some cases, the polymeric material consists essentially of cellulose units having the formula:

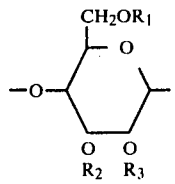

where $R_1$, $R_2$ and $R_3$ are selected from H, derivatives of $C_1$–$C_{20}$ carboxylic acid, $C_1$–$C_{20}$ alkyl groups, $C_1$ to $C_3$ monohydric and dihydric alkanols, phenyl groups, $CH_2COOH$, and $CH_2CH_2-(R_4)_3$ groups wherein $R_4 = H$, $CH_3$, or $C_2H_5$, $CH_2CH_2OH$ and $CH_2CHOHCH_3$ groups.

While specific polymers described can be used alone, they can also be used in combination with each other. For example, the lens composition can comprise a mixture of two or more different derivatives of acrylic or methacrylic acid. It is important that the ionic charge be present and that the polymer or polymer mixture provide good contact lens characteristics as known in the art such as optical clarity.

Preferably the contact lenses have a lens surface which contains ionic sites which are complexed to oppositely charged polymer sites selected from the groups COOX, $SO_3X$, and $PO_3X$, wherein $X = H$ or monovalent inorganic ion, $N+(R)_3$ groups, wherein $R = H$, $CH_3$, $C_2H_5$, $CH_2CH_2OH$ and $CH_2CHOHCH_3$ groups, $S+(R')_2$, wherein $R' = H$, $CH_3$, or $C_2H_5$ groups, $P+(R'')_3$, wherein $R'' = H$, $CH_3$, $C_2H_5$ and phenyl groups, pyridinium groups and imidazolium groups.

The lens solution forms a coating which acts to lubricate the lens. It can be used by immersing the lens in it, spraying it on a lens or other methods. It can also be used in the form of eye drops to be applied to the eye and act as an artificial tear to lubricate the lens and eye.

What is claimed is:

1. A lens solution for treating contact lens surfaces to form a protective coating thereon,
    said lens solution consisting essentially of a cationic polymer in solution with said polymer being present in an amount of from 0.001 to 10% by weight of said solution,
    said solution being useful to form protective coatings on lens surfaces formed of oppositely charged materials by producing a thin coating of a hydrogel when contacted with said contact lens surface,
    said lens solution having a pH in the range of 6 to 8.

2. A lens solution in accordance with claim 1 wherein said solution is sterile.

3. A lens solution in accordance with claim 2 wherein said lens solution has a physiologically acceptable pH and is non-irritating to the eye when used as an artificial tear.

4. A lens solution in accordance with claim 2 wherein said cationic polymer is a cellulosic polymer.

5. A sterile artificial tear solution for treating contact lens surfaces to form a protective coating thereon,
    said lens solution having a pH in the range of 6 to 8 and consisting essentially of a cationic cellulosic polymer in aqueous solution with said polymer being present in an amount sufficient to form a thin hydrogel coating on a lens surface of opposite charge.

6. A sterile lens solution for treating contact lens surfaces,
    said lens solution consisting essentially of a cationic cellulosic polymer in water solution with said polymer being present in an amount of from 0.001 to 10% by weight of said solution,
    said solution being sterile and having a physiologically acceptable pH in the range of 6 to 8.

7. A lens solution in accordance with the lens solution of claim 6 and further comprising lens cleaning and preserving additives.

8. A lens solution in accordance with claim 1 wherein said solution has the following ingredients: hydroxyethyl cellulose, benzalkonium chloride, sodium chloride, sodium bi-carbonate, disodium E.D.T.A. and water.

* * * * *